United States Patent [19]
Huang et al.

[11] Patent Number: 5,298,139
[45] Date of Patent: Mar. 29, 1994

[54] END-COLUMN CONDUCTIVITY DETECTOR FOR CAPILLARY ZONE ELECTROPHORESIS

[75] Inventors: Xiaohua Huang, Mountain View; Richard N. Zare, Stanford, both of Calif.

[73] Assignee: Board of Trustees of the Leland Stanford Junior University, Stanford, Calif.

[21] Appl. No.: 771,345

[22] Filed: Oct. 4, 1991

Related U.S. Application Data

[63] Continuation-in-part of Ser. No. 580,259, Sep. 10, 1990, Pat. No. 5,126,023.

[51] Int. Cl.⁵ ............... G01N 27/26; G01N 27/447
[52] U.S. Cl. .................. 204/299 R; 204/180.1
[58] Field of Search ............... 204/180.1, 299 R, 400

[56] References Cited

U.S. PATENT DOCUMENTS

| | | | |
|---|---|---|---|
| 4,816,123 | 3/1989 | Ogan et al. | 204/183.3 |
| 4,908,116 | 3/1990 | Zare et al. | 204/299 R |

OTHER PUBLICATIONS

Wallingford et al., "Capillary Zone Electrophoresis with Electrochemical Detection," *Anal. Chem.*, 59 (1987), 1762–1766.
Huang et al., "On-Column Conductivity Detector for Capillary Zone Electrophoresis", *Anal. Chem.*, 59 (1987), 2747–2749.
Huang et al., "Effect of Electrolyte and Sample Concentration on the Relationship between Sensitivity and Resolution in Capillary Zone Electrophoresis using Conductivity Detection", *J. Chromatogr.*, 480 (1989), 285–288.
Huang et al., "Quantitative Analysis of Low Molecular Weight Carboxylic Acids by Capillary Zone Electrophoresis/Conductivity Detection", *Anal. Chem.*, 61 (1989), 766–770.
Kuhr, "Capillary Electrophoresis", *Anal. Chem.*, 62 (1990), 403R–414R.
Foret et al., "On-Line Fiber Optic UV Detection Cell and Conductivity Cell For Capillary Zone Electrophoresis", *Electrophoresis*, 1986, 7, 430–432.
Huang et al., "Use of an On-Column Frit in Capillary Zone Electrophoresis: Sample Collection," *Anal. Chem.*, 1990, 62, 443–446.
Huang et al., "End-Column Detection for Capillary Zone Electrophoresis," *Anal. Chem.*, 1991, 63, 189–192.
Huang et al., "Current-Monitoring Method for Measuring the Electroosmotic Flow Rate in Capillary Zone Electrophoresis," *Anal. Chem.*, 1988, 60, 1837–1838.

*Primary Examiner*—John Niebling
*Assistant Examiner*—John S. Starsiak, Jr.
*Attorney, Agent, or Firm*—Majestic, Parsons, Siebert & Hsue

[57] ABSTRACT

An end-column conductivity detector is described. A sensing electrode is placed in the outlet end of a capillary that has a hole in its side wall through which electrolyte moves past the sensing electrode into a reservoir that contains the ground electrode. This structure is simple to construct, has almost no dead volume, and minimizes electrolyte contact with adhesives used to mount the sensing electrode. The end-column conductivity detector is operated in conjunction with a commercial capillary zone electrophoresis system that has a capillary cartridge and a UV absorption detector. This design thus permits sequential measurement of the absorption and conductivity characteristics of separated analyte zones. When a species can be detected by both conductivity and UV absorption, then the absorption coefficient can be determined from the relation between the conductivity signal and the concentration of the species.

12 Claims, 5 Drawing Sheets

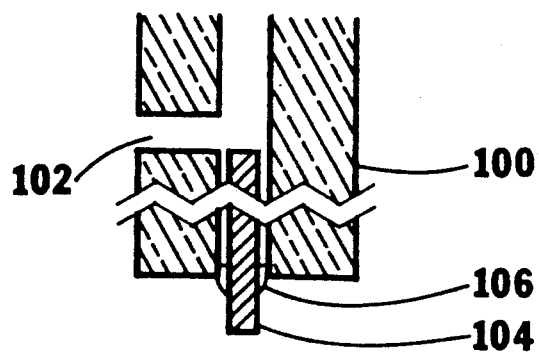
fig. —1a.
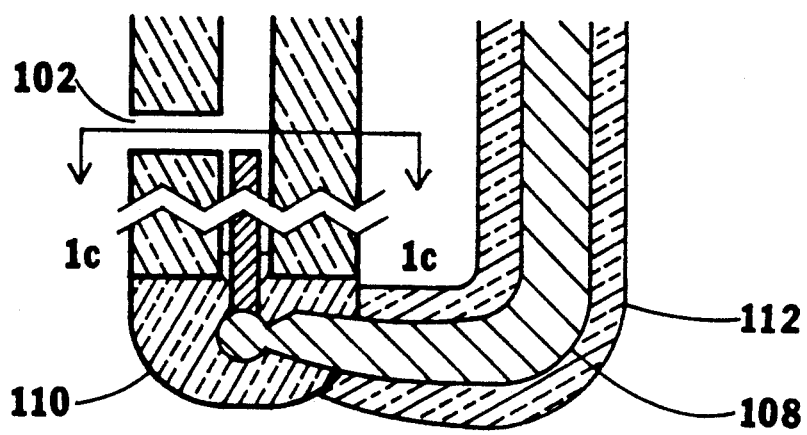
fig. —1b.
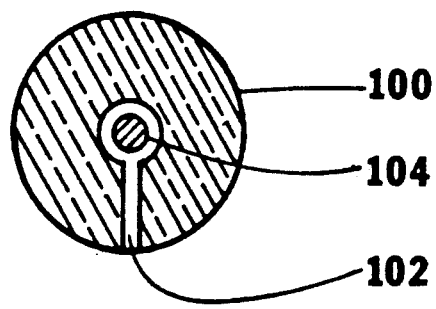
fig. —1c.

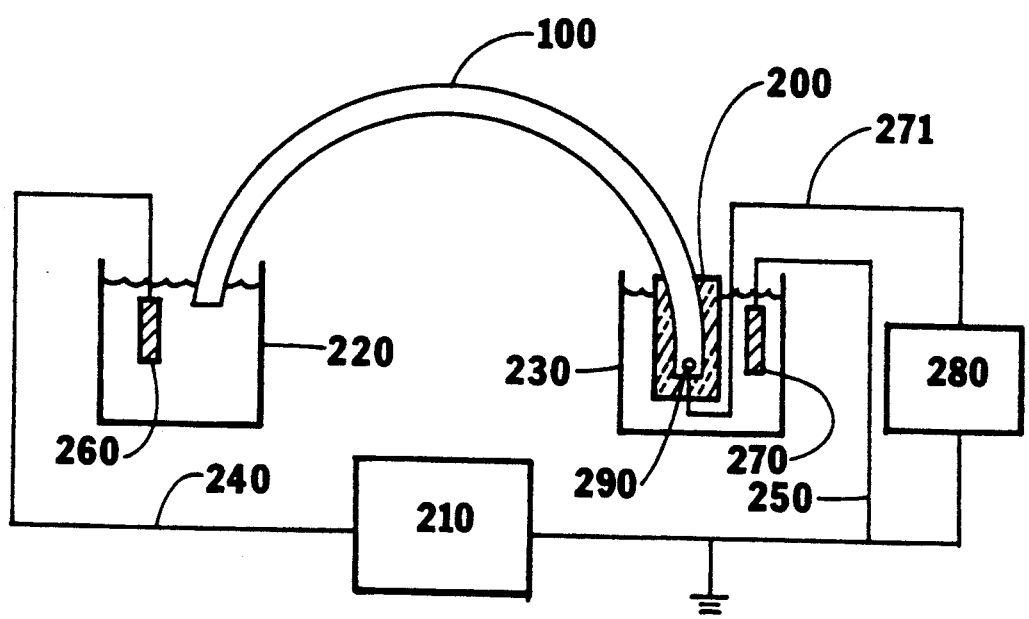
fig.—2.

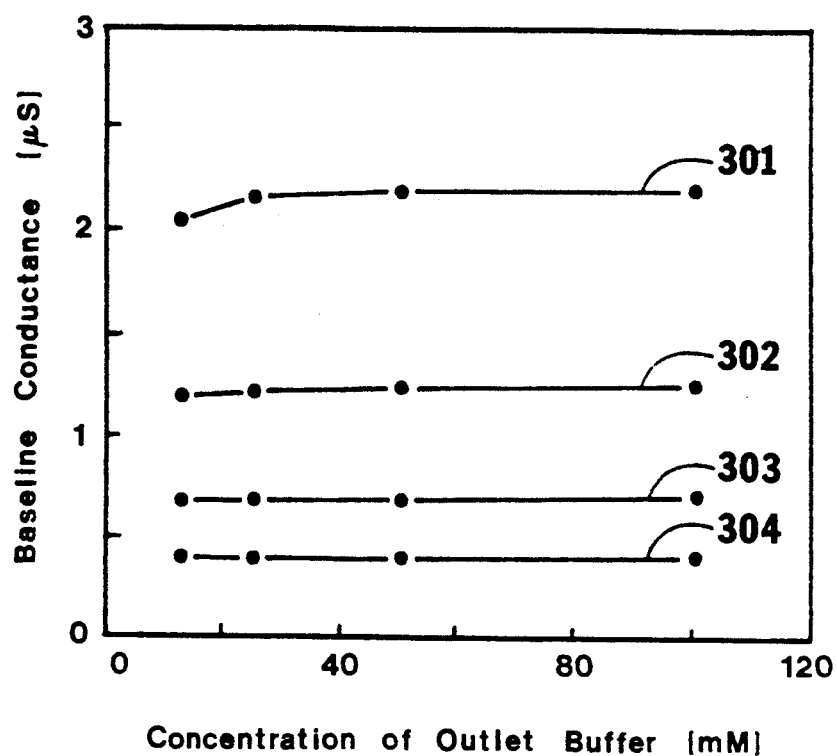
fig._3.
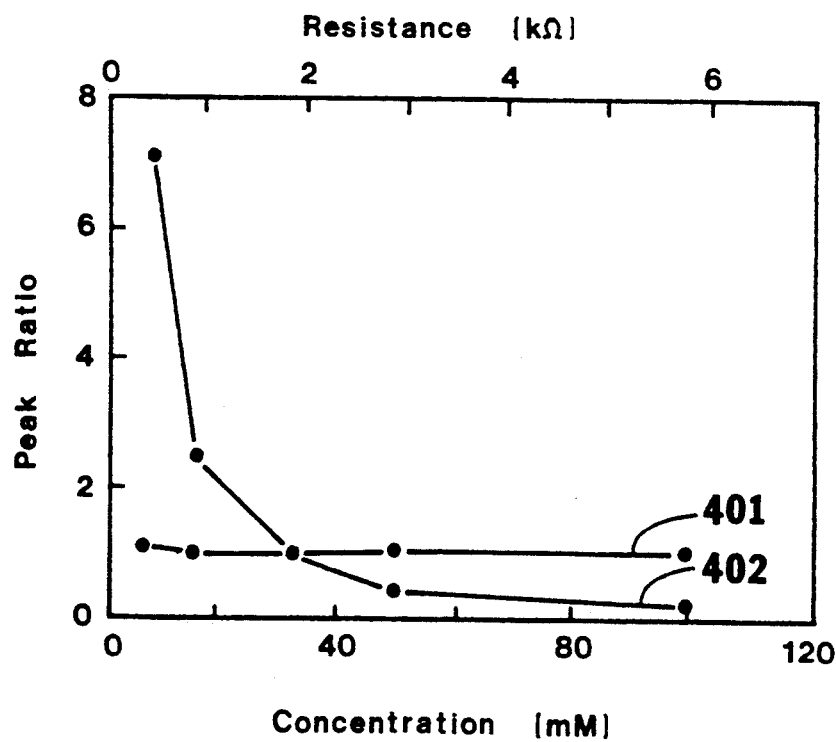
fig._4.

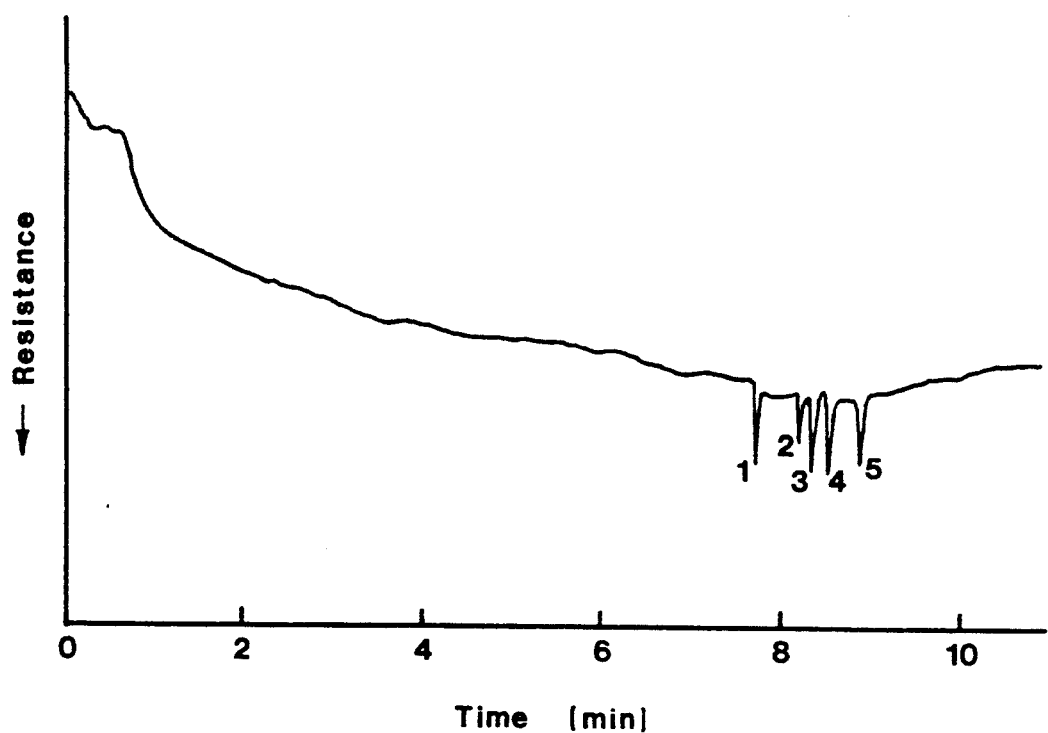
fig.—5.

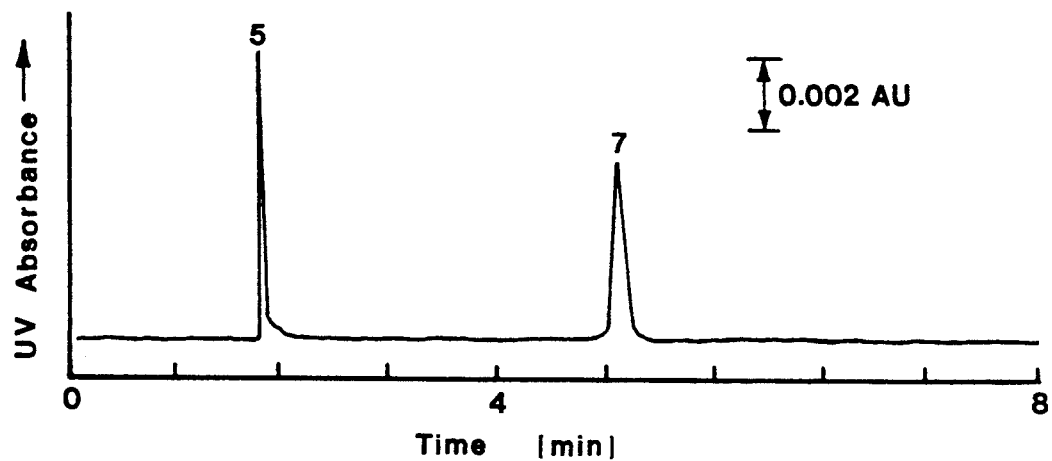
fig.—6a.
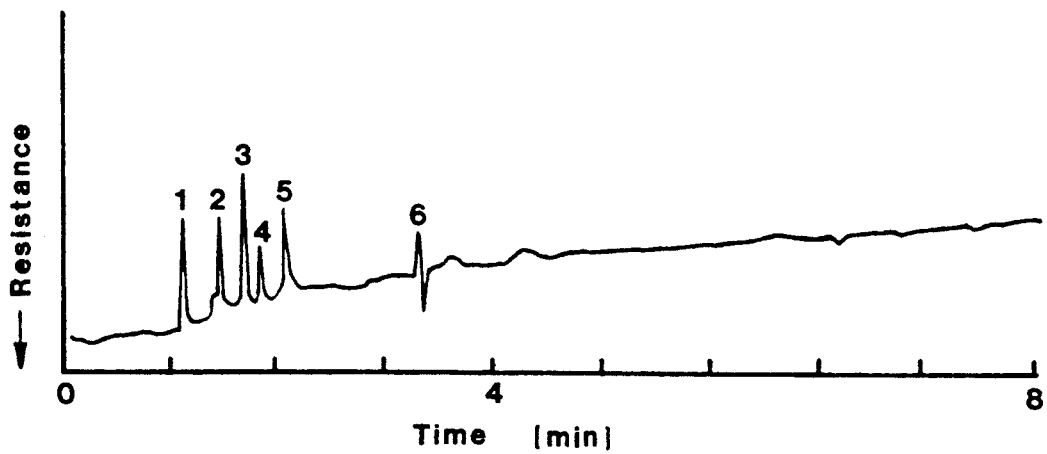
fig.—6b.

END-COLUMN CONDUCTIVITY DETECTOR FOR CAPILLARY ZONE ELECTROPHORESIS

This application is a continuation-in-part of copending application Ser. No. 580,259, filed Sep. 10, 1990 now U.S. Pat. No. 5,126,023.

FIELD OF THE INVENTION

The invention relates generally to capillary electrokinetic devices and in particular to an improved end-column conductivity detector for capillary zone electrophoresis.

BACKGROUND OF THE INVENTION

Conductivity detection is used widely in ion chromatography (Gjerde and Fritz, *Ion Chromatography*, 2nd ed., Verlag: Heidelberg, 1987; and Smith, *Ion Chromatography Applications*, CRC Press: Boca Raton, Fla., 1988), but rarely in capillary zone electrophoreses (CZE) (Kuhr, *Anal. Chem.*, 1990, 62 403R-414R). This difference apparently stems from the difficulty of fabricating a conductivity detector with low dead volume in the structure of a fused-silica capillary with an inside diameter of 100 μm or less. Three possible designs for a CZE conductivity detector are on-column, off-column, and end-column structures. Foret et al. used a microscale molding method to construct an on-column conductivity detector which was also used on-line with a UV absorbance detector (Foret et al., *Electrophoresis*, 1986, 7, 430-432). Another scheme for constructing an on-column conductivity detector employs a focused $CO_2$ laser beam to punch holes directly through the walls of the fused-silica capillary (Huang et al., *Anal. Chem.*, 1987, 59, 2747-2749). Two platinum sensing electrodes are sealed on opposite sides of the column. Because CZE typically has a voltage drop of 300 V/cm along the length of the capillary, the sensing electrodes need to be aligned carefully and an isolation transformer must be used in measuring the conductance (Huang et al., *Anal. Chem.*, 1987, 59, 2747-2749; and Everaerts et al., *Isotachophoresis, Journal of Chromatography Library* 6, Elsevier: Amsterdam, 1976).

Off-column conductivity detectors may be constructed by grounding the capillary prior to the sensing electrode, using either a porous glass structure (Wallingford and Ewing, *Anal. Chem.*, 1987, 59, 1762-1766) or an on-column frit structure (Huang and Zare, *Anal. Chem.*, 1990, 62, 443-446). Recently, Huang et al. reported the use of an end-column structure for conductimetric and amperometric detection in CZE in which the sensing electrode is placed at the outlet of the fused-silica capillary (Huang et al., *Anal. Chem.*, 1991, 63, 189-192). This end-column structure is also described in U.S. patent application Ser. No. 07/580,259, filed Sep. 10, 1990, Huang et al. Such end-column detectors demonstrate sensitivities that approach those of previous on-column conductivity detectors with only a small sacrifice in resolution, and extra band broadening of approximately 25%. This end-column structure, however, requires carefully matched microplumbing in which the analytical capillary is placed inside a second capillary that has an inside diameter slightly larger than the outside diameter of the analytical capillary. Moreover, for conductimetric detection, the end-column structure employs epoxy to help maintain structural integrity of the electrode. Unfortunately, the epoxy becomes exposed to the electrolyte which can adversely affect measurements.

SUMMARY OF THE INVENTION

It is an object of the present invention to provide end-column conductivity detectors that are easy to construct and have less dead volume.

It is another object of the present invention to provide end-column conductivity detectors that minimize the use of epoxy near the electrode and that have minimal epoxy in contact with the electrolyte.

These and other objects are achieved by the present invention which provides an end-column conductivity detector which comprises a capillary that has a hole in its side wall through which electrolytes exit into a reservoir that contains a ground electrode. A sensing electrode responsive to effluent is positioned in the bore of the capillary tube near the hole through which the effluent passes. This structure is simple to construct, has substantially no dead volume, and minimizes electrolyte contact with adhesives used to mount the sensing electrode.

The end-column conductivity detector can be mounted directly to the outlet or eluent hole of the capillary of a CZE separation system. By this means, both UV absorbance and conductivity during the same run can be recorded. The use of both detectors provides not only greater analysis power, particularly for ions that cannot readily be detected by UV absorption, but also a calibration of the UV absorbance detector. Unlike other CZE detection methods, conductivity shows a direct relationship between migration time and peak area. With the use of an internal standard, conductimetric detection allows an accurate determination of absolute concentrations in a mixture without separate calibrations for the response of each component. This unique advantage permits the UV absorption response to be calibrated on an absolute basis when both detectors are used together. Another advantage of a dual detector system is the ability to determine mobilities by sensing the sample zone as it moves by two detectors located at a known, fixed distance from each other.

BRIEF DESCRIPTION OF THE DRAWINGS

FIGS. 1a, 1b, and 1c illustrate an end-column conductivity detector.

FIG. 2 is a schematic view of a CZE separation device with an end-column conductivity detector.

FIG. 3 is a graph of the baseline conductance versus the MES/His electrolyte concentration in the outlet reservoir for different MES/His electrolyte concentrations in the capillary.

FIG. 4 is a graph of K+ peak height versus MES/His electrolyte concentration.

FIG. 5 is an end-column conductimetric electropherogram.

FIG. 6a is an UV absorbance electropherogram.

FIG. 6b is an end-column conductivity electropherogram.

DETAILED DESCRIPTION OF A PREFERRED EMBODIMENT

Construction of End-Column Conductivity Detector

As shown in FIG. 1a, a small outlet 102 (approximately 40 μm in diameter) is drilled through the wall 100 of a fused-silica capillary, approximately 50 to 75 μm inside diameter and approximately 360 μm outside diameter (Polymicro Technologies, Phoenix, Ariz.) using the focused output of a home-built, computer-controlled $CO_2$ laser (10.6 μm, Model RF 165, Laakmann, San Juan Capistrano, Calif., 40 W max.). A capillary or capillary tube as referred to herein typically has an inner diameter of about 500 μm or less. The distance from the outlet 102 to the end of the capillary is approximately 7 mm. A platinum or stainless steel 50 μm-diameter wire 104 (California Fine Wire Co., Grover City, Calif.) is inserted along the length of the capillary. The tip of this wire is placed close to but not protruding into the hole structure. This wire, which serves as the sensing electrode, is sealed to the capillary outlet using epoxy adhesive 106 (Torrseal, Varian, Lexington, Mass.). In the embodiment as shown in FIG. 1a, the sensing electrode diameter is less than the inner diameter of the capillary so that a small dead volume filled with electrolyte is present between the electrode and the inner capillary wall. The presence of the dead volume does not adversely affect the performance of the inventive device. The dead volume can be eliminated by filling the gap with epoxy. Alternatively, a larger diameter electrode may be chosen so that the sensing electrode is closely-fitted to the inner capillary wall thereby substantially eliminating any dead volume.

During separation, samples migrate from the inlet to the outlet thereby defining the direction along the tube that is away from inlet and towards the outlet as being downstream. The tip of the electrode faces the effluent as it moves downstream towards the small hole 102. As shown in FIG. 1b, a fine, insulated lead wire 108 (#30 wire wrap, Page Digital Electronics, Duarte, Calif.) is connected to the sensing electrode. Insulator 110 lowers the tip of the capillary thereby enclosing the electrode-lead wire connection. Lead wire 108 is covered with insulation 112. FIG. 1c presents a cross—sectional view of this end-column conductivity detector.

While the inventive conductivity detector as described herein is used with CZE, the inventive device can be readily adapted with other formats of capillary electrophoresis including capillary isotachophoresis and gel electrophoresis.

FIG. 2 shows a CZE separation system with an end-column conductivity detector. A reversible high voltage power supply 210 provides a variable voltage of 0–30 kV with the outlet of the separation capillary 100 at ground potential. The capillary is liquid-filled with an electrolyte and terminates inside protective jacket 200. Inlet reservoir 220 and outlet reservoir 230 contain electrolyte as well, so that the liquid-filled capillary 100 creates a continuous liquid and electrical connection between them. Protective jacket 200 with a large hole 290 (>1 mm in diameter) that is aligned with the small hole 102 (not shown) is attached to capillary tube 100. This protective jacket provides an outlet for the eluent and gives structural support to the capillary. The outer diameter of the capillary is approximately 360 μm and the inner diameter of the capillary is approximately 75 μm. The structure is placed inside outlet reservoir 230 that contains ground electrode 270. An effective electrokinetic voltage is supplied from power supply 210 through conductors 240 and 250 and grounding electrode 270 and electrode 260.

The conductivity is measured between the sensing and the ground electrodes, using a home-made AC circuitry operated at 3.5 kHz. The output of the end-column conductivity detector is passed through lead 271 to conductivity meter 280 and is recorded. (See, Huang et al., *Anal. Chem.*, 1987, 59, 2747-2749; and Everaerts et al., *Isotachophoresis, Journal of Chromatography Library* 6, Elsevier: Amsterdam, 1976.) In some studies, an end-column conductivity detector is mounted directly on the end of the capillary from the cartridge of a commercial CZE separation systems, (e.g., P/ACE TM 2000, Beckman Instruments, Inc., Palo Alto, Calif.) thereby allowing the use of dual detection, UV absorbance and conductivity, under microprocessor control.

Reagents and Samples

All chemicals are from Sigma Chemical Corp. (St. Louis, Mo.) and are not further purified. Water used to prepare solutions is freshly deionized and distilled with a water purifier (Model LD-2A) coupled with a Mega-Pure Automatic Distiller (Corning Glassworks, Corning, N.Y.). Electrolyte solutions are filtered through a 0.2-μm membrane (Acrodisc, Gelman Scientific, Inc., Ann Arbor, Mich.). Buffers are prepared with 2-morpholinoethanesulfonic acid (MES) and equimolar histidine (His) (3–100 mM). Phosphate buffer and potassium acetate buffer, with the pH adjusted as needed, were also used.

RESULTS AND DISCUSSION

Variation of Response with Placement of Sensing Electrode

The performance of the end-column conductivity detector was examined as the position of the sensing electrode was changed relative to the eluent hole. The inlet of the capillary was immersed in a reservoir at high positive voltage (anode), and the outlet of the capillary was immersed in a reservoir at ground potential (cathode). The current through the capillary was recorded using a current-sampling resistor (Huang et al., *Anal. Chem.*, 1988, 60, 1837-1838). Two kinds of buffers, MES/His (10 mM, pH 6.1) and phosphate (20 mM, pH 7.0), were employed to test the low- and high-current regimes, respectively. The position of the sensing electrode was adjusted using a microscope with a 5× objective. Four positions were studied: (1) with the flat tip of the sensing electrode protruding past the center of the eluent hole; (2) with the tip at the center of the eluent hole; (3) with the tip on the edge of the eluent hole (or even therewith), as shown in FIG. 1a, in this position the tip is said to be "flush" with the edge of the eluent hole furthest away from the inlet and downstream from the inlet; and (4) with the tip recessed 100 μm from the edge of the eluent hole.

For positions 1 and 2, the current fluctuated wildly after 1 to 2 minutes and then declined when high voltage (300 V/cm) was applied. It is believed that gas bubbles accumulating around the sensing electrode caused this undesirable behavior. For positions 3 and 4 the current was stable. No significant difference in current was observed between capillaries with a sensing electrode in positions 3 or 4 and those with no sensing electrode. Results of a study of the electroosmotic flow rate also suggested that the sensing electrode in positions 3 or 4 caused no interference in the operation of the capillary. Position 4 had an extra segment of liquid in front of the sensing electrode, and this liquid increased the resistance of the conductivity circuit. For this reason, the embodiment of position 3 (shown in FIG. 1a) is generally preferred.

Variation of Response with Differences in Electrolyte Between the Capillary and the Outlet Reservoir Conductivity is measured between the sensing electrode, located inside the capillary near the capillary's outlet, and the ground electrode, located inside the outlet reservoir. FIG. 3 shows the results of a study of how the baseline conductivity varies with the concentration of MES/His buffer in the outlet reservoir when the electrolyte inside the capillary is 100 mM (curve 301), 50 mM (curve 302), 25 mM (curve 303), and 12.5 mM MES/His (curve 304). It appears that a change in the concentration of the electrolyte in the outlet reservoir hardly affects the baseline conductivity. On the other hand, the baseline conductivity changes linearly with a change in the concentration of the electrolyte inside the capillary. The only possible exception to this generalization is when high-concentration electrolyte inside the capillary enters the outlet reservoir containing low-concentration electrolyte. This study indicates that reliable conductivity measurements can be achieved without the interference of what might be called "memory effects" from sample zones that have passed by the sensing electrode. The outlet reservoir has about a million times the volume of the capillary. Thus, with the present invention the outlet reservoir serves as a giant ground electrode that is not influenced by the tiny changes of what flows into it.

FIG. 4 shows the influence of electrolyte concentration ($K^+$ cation at $5 \times 10^{-4}$M) on peak height as the electrolyte concentration is changed in the outlet reservoir (curve 401) and in the capillary (curve 402). Note that a change in the electrolyte concentration inside the capillary from 100 mM to 5 mM causes the $K^+$ peak height to increase by a factor of 100, whereas the same change of electrolyte concentration in the outlet reservoir causes no detectable change in the peak height. The same behavior has been observed in CZE with an on-column conductivity detector (Huang et al., *J. of Chromatography*, 1989, 480, 285-288). FIGS. 3 and 4 demonstrate that the present end-column conductivity detector has similar characteristics to the previously described conductivity detector in Huang et al., *Anal. Chem.*, 1991, 63, 189-192 (Huang et al., *Anal. Chem.*, 1987, 59, 2747-2749; and Huang et al., *Anal. Chem.* 1989, 61, 766-770).

Potential Drop Between the Sensing and the Ground Electrodes

One feature that distinguishes the end-column from the on-column conductivity detector is the size of the potential drop. If the sensing electrode in the on-column detector is 5 cm from the capillary outlet, the sensing electrode is at 1500 V with respect to ground, assuming a potential of 300 V/cm. Because the sensing electrode in the end-column detector is much closer to the outlet of the capillary, the potential drop should be much smaller. (The outlet of the inventive conductivity detector is the hole 102 as shown in FIG. 1a. A homemade, high-impedance DC voltage meter was used to measure directly the potential on the sensing electrode. The potential difference was found to be approximately 6 V under our experimental conditions (300 V/cm, 20 mM phosphate buffer, pH 7.0). Moreover, the potential drop was linear with applied electric field. These results suggest that an extra resistance occurs between the sensing and ground electrodes. At an applied electric field of 300 V/cm, a potential drop of 6 V is equivalent to an electrolyte segment of 0.2 mm length with the same diameter as the inside diameter of the capillary (75 μm). It is believed that this extra resistance arises primarily from the eluent hole, which suggests that the resistance can be lowered by expanding the cross-sectional area and decreasing the length of this hole.

Because only a few volts difference occurs between the sensing and ground electrodes, a specially designed, isolated conductivity meter such as was used previously is unnecessary (Huang et al., *Anal. Chem.*, 1987, 59, 2747-2749; and Huang et al., *Anal. Chem.* 1989, 61, 766-770). Instead, capacitors to couple the end-column conductivity detector to the AC conductivity meter were used. Although the voltage drop is small, it is still large enough to cause formation of gas bubbles. Evidently, bubbles are not a serious problem, perhaps because the flowing liquid suppresses build up. Alternatively, the inventive end column detector can be used as a DC potential detector.

Zone Broadening

The peak width of pyridoxamine using both the UV absorbance and the end-column conductivity detector (modified P/ACE 2000 system) was measured. The UV absorbance detector was located 58 mm prior to the conductivity detector. Based on half-height measurements but with no correction for the spread of the zone with time and length, the extra zone broadening is estimated to be less than 15% for the end-column conductivity detector, based on eight separate measurements. Hence, the end-column conductivity detector introduces little loss in resolution.

A further indication of this fact is the number of theoretical plates obtained using the end-column conductivity detector. FIG. 5 shows an electropherogram of 5 different metal ions, each at a concentration of approximately $5 \times 10^{-5}$M (20 nL injection). Peaks 1, 2, 3, 4, and 5 correspond to $Ca^{2+}$, $Na^+$, $Mg^{2+}$, $Ni^{2+}$, and $Cd^{2+}$, respectively. The running buffer is 5 mM potassium acetate, pH 5.0. The applied electric field is 200 V/cm. This separation was not optimized; better sensitivity and higher resolution could be achieved. In this electropherogram, the $Cd^{+2}$ cation has a peak width that corresponds to 150,000 theoretical plates.

Application of Dual Detection Systems

Using the P/ACE 2000 system equipped with the end-column conductivity detector, both the UV absorbance and the conductance as a function of time after a sample of a complex mixture was injected were recorded. The running buffer is 5 mM MES/His, pH 6.0; applied voltage = 15 kV; 30 cm to the UV absorbance detector; 35.8 cm to the end-column conductivity detector; temperature = 25.0°±0.10° C. These identifications were confirmed by a series of spiking experiments.

The complex mixture included $K^+$, $Na^+$, $Li^+$, pyridoxamine, and the dansyl-isoleucine salt of cyclohexamine. In these measurements as shown in FIG. 6, the peaks correspond to the different ions and molecules as follows: $K^+$ (1), $Na^+$ (2), $Li^+$ (3), cyclohexamine (4), pyridoxamine (5), $H_2O$ (6), and dansyl-isolencine (7). Peaks 1, 2, 3, and 7 are $\sim 1 \times 10^{-4}$M; peak 5 is $2.5 \times 10^{-4}$M. Peak 4 (cyclohexamine) is associated as the salt of peak 7 (dansyl-isolencine). In the UV absorbance electropherogram (λ=254 nm) (FIG. 6a), only pyridoxamine and dansyl-isoleucine can be identified, whereas in the conductimetric electropherogram (FIG. 6b) six peaks can be observed that correspond to $K^+$, Na+, Li+, cyclohexamine, pyridoxamine, and a water peak. Because the end-column conductivity detector is 58 mm after the UV absorbance detector, the two electropherograms are offset in time; the UV absorbance peak always precedes the conductivity peak of the same species.

Note that K+, Na+, Li+, cyclohexamine, and the $H_2O$ peak appear only in conductivity, the dansyl-isoleucine only in UV absorbance, and the pyridoxamine in both detection schemes. The dansyl-isoleucine might have been expected to be detected in conductivity, yet because MES has a similar conductivity under these operating conditions, the dansyl-isoleucine probably escapes detection by conductivity measurements. The UV absorption detector yields a nearly flat baseline, whereas the conductivity detector has a characteristic, curved baseline at early time, which reduces its sensitivity. Nevertheless, the simultaneous recording of these two different characteristics of an analyte zone can aid in the analyte's identification and quantitation.

The use of an internal standard in CZE/conductivity detection permits quantitative analysis of the composition of a mixture without the need to make calibration curves of the detector response for the species present (Huang et al., *Anal. Chem.* 1989, 61, 766–770). The inventive end-column conductivity detector is particularly well suited for this detection scheme as it is simple to construct, has small extra zone broadening, avoids epoxy adhesive near the tip of the sensing electrode, and can be operated without isolation transformers.

It is to be understood that while the invention has been described above in conjunction with preferred specific embodiments, the description and examples are intended to illustrate and not limit the scope of the invention, which is defined by the scope of the appended claims.

It is claimed:

1. A method of fabricating an end-column detector for electrophoresis which comprises the steps of:
   providing an elongated tube having a sidewall and a first opening and a second opening that are in fluid communication with a bore within the tube wherein the bore is defined by an inner surface of the tube;
   drilling an eluent hole through said tube sidewall between the first and second opening so that the the eluent hole is in fluid communication with said bore;
   inserting an elongated sensing electrode having a tip through the second opening so that the tip is adjacent to said eluent hole; and
   sealing the second opening between the inner surface of the tube and sensing electrode.

2. The method of fabricating an end-column detector as defined in claim 1 wherein the step of sealing the second opening comprises applying adhesive to the second opening between the tube inner surface and the sensing electrode whereby the adhesive forms a seal located at the second opening that is away from the aperture.

3. The method of fabricating an end-column conductivity detector as defined in claim 1 wherein the step of inserting the sensing electrode through the second opening comprises positioning the elongated electrode through said second opening and closely-fitting the electrode to the inner surface.

4. The method of fabricating an end-column conductivity detector as defined in claim 1 wherein the step of drilling the eluent hole comprises forming a small hole through the tube sidewall wherein the hole is in fluid communication with said bore.

5. An electrophoresis column and sensor assembly comprising:
   an elongated tube having a wall defining a bore, said tube having an inlet, said tube further having an eluent hole through the wall in fluid communication with the bore, wherein separated sample components migrate from the inlet through the bore and exit through the eluent hole; and
   a sensing electrode extending into the bore having a tip facing towards oncoming component migration wherein the tip is positioned in proximity to the eluent hole and whereby the components migrate past the tip of the sensing electrode and exit the bore through the eluent hole in the wall.

6. The electrophoresis column as defined in claim 5 further comprising means for causing electrophoresis of a sample placed in the bore whereby the sample is separated into components.

7. The electrophoresis column as defined in claim 6 wherein the eluent hole has an inner aperture that is downstream from said inlet, downstream referring to a direction along the tube that is away from the inlet, and wherein the tip of the sensing electrode is positioned in proximity to the aperture.

8. The electrophoresis column as defined in claim 7 wherein said sensing electrode tip is substantially flush with an aperture edge that is furthest from said inlet.

9. The electrophoresis column as defined in claim 8 wherein said aperture has a diameter of approximately 2 to 200 $\mu$m.

10. The electrophoresis column as defined in claim 6 wherein the sensing electrode has an elongated structure and wherein the column further comprises adhesive means between said elongated structure and said tube wall for sealing the elongated structure to the wall.

11. The electrophoresis column as defined in claim 6 wherein the sensing electrode has an elongated structure and wherein the dimensions of the elongated electrode are such that the sensing electrode closely fits to the wall of the tube.

12. The electrophoresis apparatus as defined in claim 5 further comprising an absorption detector.

* * * * *